United States Patent
Harders et al.

(10) Patent No.: US 11,628,278 B2
(45) Date of Patent: *Apr. 18, 2023

(54) SECUREMENT DEVICE FOR POLYMER TUBING AND POLYMER COATED CABLES

(71) Applicant: BioDerm, Inc., Largo, FL (US)

(72) Inventors: James Alan Harders, Santa Barbara, CA (US); Steve J. Babb, Seminole, FL (US); David W. Underwood, Tampa, FL (US); Dennis M. Kay, Largo, FL (US)

(73) Assignee: BioDerm, Inc., Largo, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/855,494

(22) Filed: Jun. 30, 2022

(65) Prior Publication Data

US 2022/0331561 A1 Oct. 20, 2022

Related U.S. Application Data

(63) Continuation of application No. 16/653,342, filed on Oct. 15, 2019, now Pat. No. 11,376,402, which is a continuation of application No. 15/420,592, filed on Jan. 31, 2017, now Pat. No. 10,485,955, which is a continuation-in-part of application No. 14/024,963, filed on Sep. 12, 2013, now abandoned, which is a continuation of application No. 12/620,844, filed on Nov. 18, 2009, now abandoned.

(51) Int. Cl.
*A61M 25/02* (2006.01)

(52) U.S. Cl.
CPC ....... *A61M 25/02* (2013.01); *A61M 2025/024* (2013.01); *A61M 2025/0266* (2013.01)

(58) Field of Classification Search
CPC ............ A61M 25/02; A61M 2025/026; A61M 2025/0266; A61M 2025/0206; A61M 2025/0253; A61M 5/1418; A61M 2025/0273

See application file for complete search history.

(56) References Cited

U.S. PATENT DOCUMENTS

| | | | | |
|---|---|---|---|---|
| 4,477,950 A | * | 10/1984 | Cisek | B65D 63/1027 24/17 AP |
| 4,662,873 A | * | 5/1987 | Lash | A61M 25/02 604/179 |
| 5,685,859 A | * | 11/1997 | Kornerup | A61M 1/90 604/179 |
| 2003/0125668 A1 | * | 7/2003 | Bierman | A61M 25/02 604/174 |

(Continued)

*Primary Examiner* — Emily L Schmidt
(74) *Attorney, Agent, or Firm* — Hill Ward Henderson, P.A.; Stephen E. Kelly

(57) ABSTRACT

A securement device for catheter tubes and polymer coated cables includes a base mounted on a support surface, and male and female straps, the male straps having locking members that mate with corresponding apertures in the female straps. The male and female straps connect to a base via fixed ends of the respective male and female straps, and each of the fixed ends comprises a curved portion configured to orient the corresponding unsecured strap substantially parallel to the base. Each of the fixed ends of the male straps mate with the fixed ends of the corresponding female strap, thereby forming a crease for seating the tube or cable being secured.

20 Claims, 12 Drawing Sheets

(56) References Cited

U.S. PATENT DOCUMENTS

2006/0041233 A1* 2/2006 Bowen ............... A61M 25/02
604/180
2009/0326474 A1* 12/2009 Bierman ............ A61M 5/1418
604/180
2012/0016312 A1* 1/2012 Brown ............... A61M 25/02
604/174

* cited by examiner

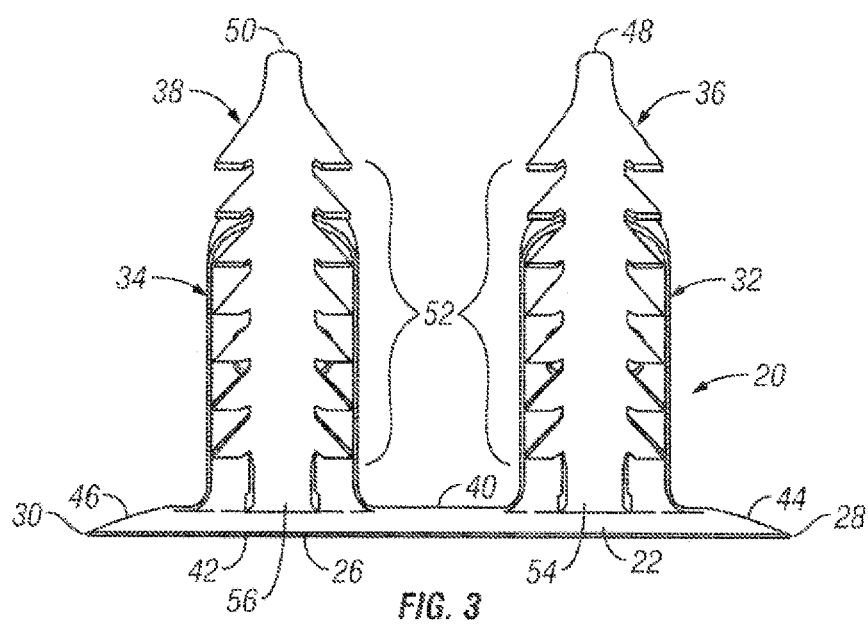
FIG. 3
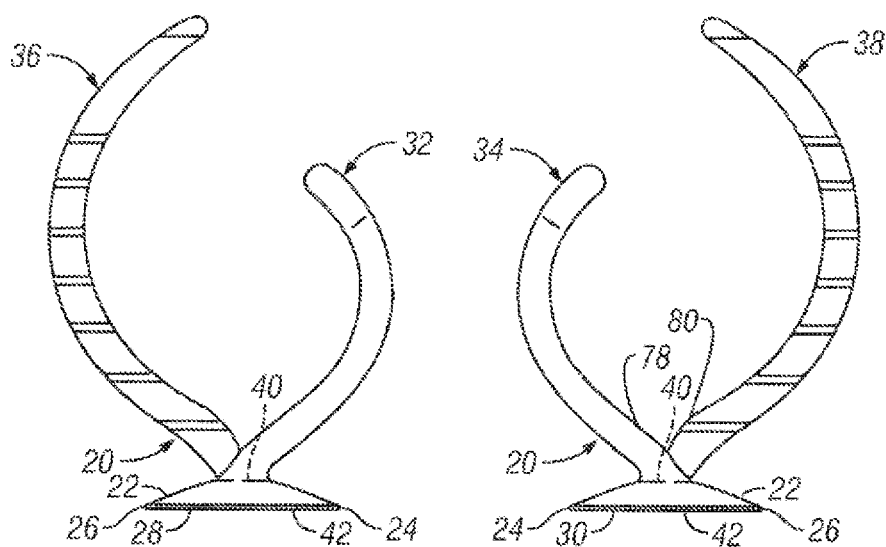
FIG. 4
FIG. 5

SECUREMENT DEVICE FOR POLYMER TUBING AND POLYMER COATED CABLES

CROSS-REFERENCED TO RELATED APPLICATION

This application is a continuation of U.S. patent application Ser. No. 16/653,342, filed on Oct. 15, 2019, which is a continuation of U.S. patent application Ser. No. 15/420,592, filed on Jan. 31, 2017, which is a continuation in part of U.S. patent application Ser. No. 14/024,963, filed on Sep. 12, 2013, which is a continuation of U.S. patent application Ser. No. 12/620,844, filed Nov. 18, 2009, the entire contents of each of which are incorporated herein by this reference.

BACKGROUND

(1) Field of the Invention

The tube holder described herein pertains to devices and methods for securing elongate members, such as medical tubing, and more particularly, to methods and devices utilizing a tube holder to secure catheters to a patient's body.

(2) Description of Related Art

Medical catheters are used to transfer liquids and gases (fluids) to and/or from naturally or surgically created openings such as stoma, the oral cavity, the urethra or percutaneous central sites such as for venous catheters. Catheter safety and reliability depend on assuring patency of the lumen of the catheter and securement such that physical forces are not transmitted internally to the patient. Design and materials of a catheter tube holder are needed so as to not cause injury to the patient, such as maceration, pressure ulcers, skin tears and infections for example.

Catheters commonly range in size from 1.9 French ("Fr") (approximately 0.627 mm) for neonatal applications through thoracostomy tubes up to and beyond 44 Fr (approximately 14.52 mm) and include many varieties of mid-size catheters (for example, intravenous, suprapubic, urinary drainage, etc.). To reduce caregiver training costs and improve catheter securement and insertion site dressing technique compliance, a safe and reliable catheter tube holder is desirable which can be used for the entire range of commonly used catheters.

One of the disadvantages of prior art catheter securement devices (tube holders) is that such catheter securement devices permit in-and-out motion or "pistoning" of catheters at the point of entry (insertion site) into a patient's body, and even slight in-and-out motion or "pistoning" can cause infection in that the sliding movement of a catheter with respect to an insertion site carries organisms (pathogens) through the epidermal barrier to cause such infections. Such sliding movement is not adequately prevented by medical tape and catheter holders or securement devices currently available.

The walls of catheters are typically subject to various physical forces which are potentially detrimental to the patency of the catheter lumen and may cause tissue injury to a patient. Polymeric materials used for catheter construction typically exhibit a high flexural modulus, softness (i.e. low durometer) and high modulus of elasticity resulting in catheters which are pliable but resist stretch. Conventional polymeric materials include silicone rubber and various thermoplastic elastomers such as polyisobutylene (latex), polyvinylchloride (PVC), fluorinated ethylene proprylene (FEP), polytetrafluoroethylene (PTFE) and polyurethane. Material properties which make catheters pliable also render the catheters susceptible to crushing such as at rigid pinch points in various prior art catheter securement devices. Kinking is another factor which can cause significant loss of catheter patency such as when a catheter is forced to bend excessively over a short distance.

Catheters are also subject to twisting forces along the longitudinal axes thereof caused by the arrangement of other medical devices or patient movement. Catheters are also subject to tugging and leverage forces caused by various factors such as bending at the catheter insertion site into a body. Prior art catheter securement devices do not adequately protect against the above-mentioned disadvantages such that tissue damage can occur wherever a patient's skin is crushed or torn (ischemia) and also do not permit a controlled and stable angle of entry at the insertion site for a catheter to avoid near 90° entry of the catheter at the insertion site which can allow leverage forces to be transmitted through the catheter thereby causing crushing at the outboard interface and tearing at the inboard interface. Detrimental leverage forces also occur with the use of catheter securement devices having a swiveling gripping design.

SUMMARY

One aspect of the securement device is to provide a medical tubing arrangement (e.g. for catheters) positively gripping the tubing for avoiding the above-described disadvantages of the prior art relating to physical forces encountered in clinical practice for the normal range of catheter sizes.

In another aspect, the securement device incorporates a tube holder providing standardized, positive gripping of catheters of various sizes with a support surface in the form of an elastic skin attachment foundation pad capable of stretching over swollen tissue (edema or anasarca) while maintaining excellent adhesion over complex body surfaces or curvatures which can change continuously due to body movement or repositioning.

A further aspect of the securement device is to provide a tube holder that firmly grips catheters of varying sizes to reduce "tug trauma", i.e. gradual or sudden breaking of the skin/adhesive bond encountered when semi-or fully-rigid securement devices do not stretch with natural skin movement which can cause an adhesive bond to shear.

In an additional aspect, a tube holder utilizes male and female straps with the female straps having a plurality of apertures therein for receiving locking members carried by a male strap such that, dependent upon the aperture into which locking members of the male strap are inserted, the tube holder can firmly grip catheters of varying sizes.

In an additional aspect, a tube holder includes a female strap having a plurality of apertures therein with the aperture closer to a base of the tube holder having a height less than the height of the other apertures thereby facilitating a gripping of small diameter tubes by flexible locking members carried by a male strap extending through the smaller aperture.

Another aspect of the securement device is to firmly grip various size tubes with first and second gripping members of a tube holder by configuring one of the gripping members to have an configuration defining an engagement portion to cooperate with an engagement portion of the other gripping member to securely hold the tubes with jaws in a "channel lock" manner.

In a further aspect, the tube holder utilizes a base with a raised curved or dome-like platform to form a shock-absorbing and isolating structure mounting male and female straps for gripping tubes.

Some of the advantages of the securement device over prior art tube holder/catheter securement arrangements include increased securement (gripping) of tubes, increased infection control, cooperation with skin physiology to reduce injuries, safety in use due to elimination of structures which could cause tissue cuts, maceration or necrosis, easier training of caregivers and use by caregivers due to standardization (i.e. single tube holder for various size catheters), protection of lumen patency across a wide range of catheter dimensions, materials and clinical applications, reduction of the potential for infection due to the ability to create an occlusive seal against pathogens and/or prevention of catheter dislodgement.

In one embodiment, the male and female straps connect to a base via fixed ends of the respective male and female straps, and each of the fixed ends comprises a curved portion configured to orient the corresponding unsecured strap substantially parallel to the base. Each of the fixed ends of the male straps mate with a recess in the fixed ends of the corresponding female strap, thereby forming a crease for seating the tube or cable being secured.

In one embodiment, each of the plurality of locking members attached to the male straps comprises a root, a tip, a leading edge, and a notch in the root.

Other aspects and advantages of the securement device will become apparent from the following description of the invention taken in conjunction with the accompanying drawings, wherein like parts in each of the several figures are identified by the same reference characters.

BRIEF DESCRIPTION OF THE DRAWINGS

FIGS. 2 and 3 are opposite side views, respectively, of the tube holder of FIG. 1.

FIGS. 4 and 5 are opposite end views, respectively, of the tube holder of FIG. 1.

DETAILED DESCRIPTION OF THE PREFERRED EMBODIMENTS

Figure 1:
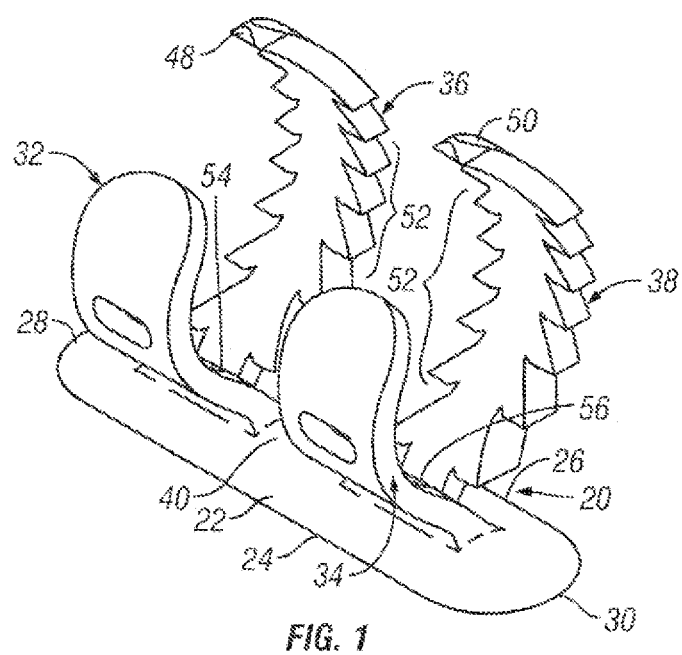
FIG. 1 is a perspective view of one embodiment of the tube holder.

With reference to the drawings, the securement device will now be described with regard for the best mode and the preferred embodiments. In general, the device disclosed herein is a device for securing a tube or a polymer coated cable to a patient's body or other secure article. The embodiments disclosed herein are meant for illustration and not limitation of the inventive scope. An ordinary practitioner will appreciate that it is possible to create many variations of the following embodiments without undue experimentation.

As used herein, the term "tube" means an elongate member (i.e. a member having a length greater than its diameter/width) regardless of the cross-sectional configuration thereof (e.g. round, circular, oval, curved, three or more sided, polygonal or the like). The "tube" can be hollow or partially hollow or can be constituted by a tubular coating on an object such as a metal wire or can be formed of a slotted sleeve, such as a catheter support sleeve. As used herein, the term "body" means a corpus, such as of an animal or a human, or a part thereof such as skin or an appendage.

One embodiment of the tube holder 20, as shown in FIGS. 1-5, includes an elongated base 22 having opposing lateral sides or edges 24 and 26 and 26 defines a width for the base and the spacing between ends 28 and 30 defines a length for the base with the length being greater than the width. Extending substantially transversely from the base are gripping members in the form of female straps 32 and 34 and gripping members in the form of male straps 36 and 38 in lateral alignment with female straps 32 and 34, respectively. The female straps are longitudinally spaced along the base, and the male straps are similarly longitudinally spaced along the base such that the male straps 36 and 38 are in opposed alignment with the female straps 32 and 34, respectively, forming pairs of gripping members 32,36 and 34,38.

The base 22 has a central domed platform 40 raised above a substantially flat bottom surface 42 to form a shock absorbing and isolating structure upon which the male and female straps are mounted. The flat bottom surface 42 of the base 22 extends widthwise entirely across the width of the base, and the raised platform 40 has a domed upper surface spaced from the bottom surface 42 with the width of the platform being less than the width of the base. The male and female straps extend arcuate from the lateral sides of the platform to curve laterally and upwardly away from the base. The longitudinal ends 28 and 30 of the base have surfaces 44 and 46, respectively, sloping from the upper surface of the platform 40 to the bottom surface 42 of the base at an angle on the order of 21° to accommodate the preferred angle of entry for catheters into a patient's body thereby reducing upward forces or leverage that would occur if the base had transversely extending (square) longitudinal ends. The sloping surfaces 44 and 46 support catheter tubes as the tubes extend toward the body of a patient from the platform 40.

Figure 8:
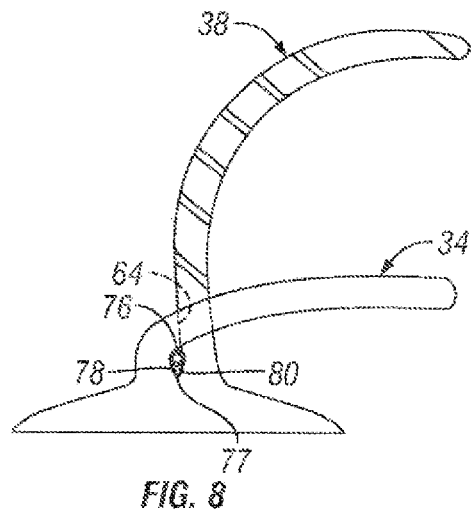
FIG. 8 is an end view showing the tube holder of FIG. 1 gripping a small tube.
Figure 9:
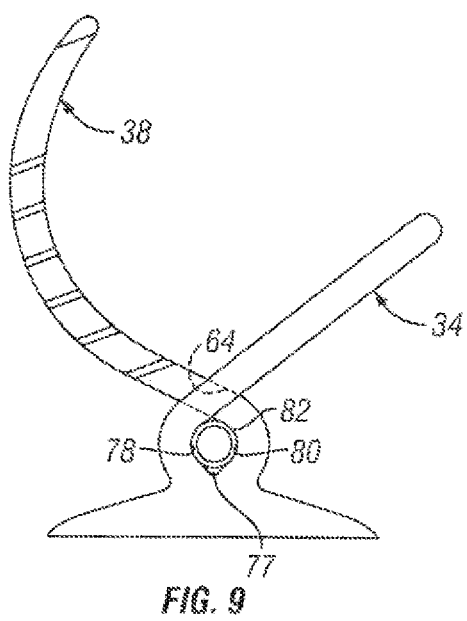
FIG. 9 is an end view showing the tube holder of FIG. 1 gripping an intermediate size tube.
Figure 10:
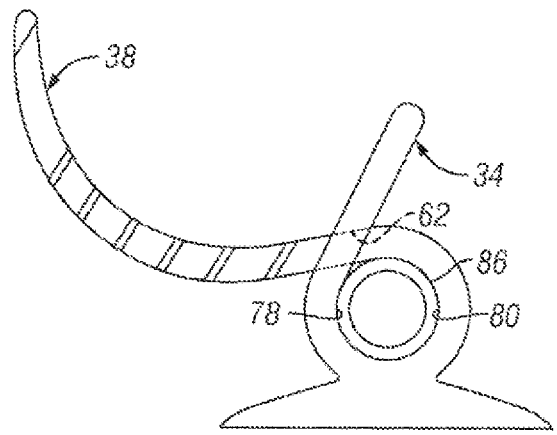
FIG. 10 is an end view showing the tube holder of FIG. 1 gripping a large tube.
Figure 11:
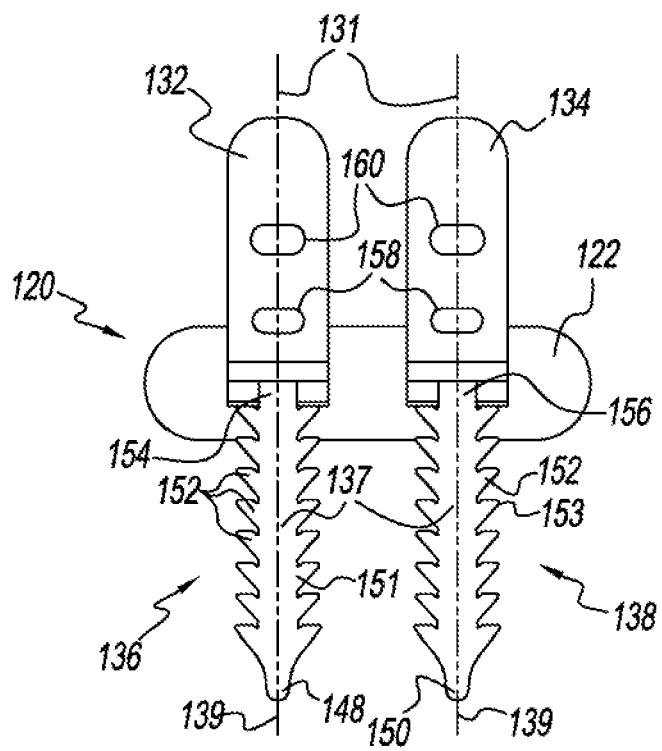
FIG. 11 is a top view of one embodiment of a securement device.
Figure 12:
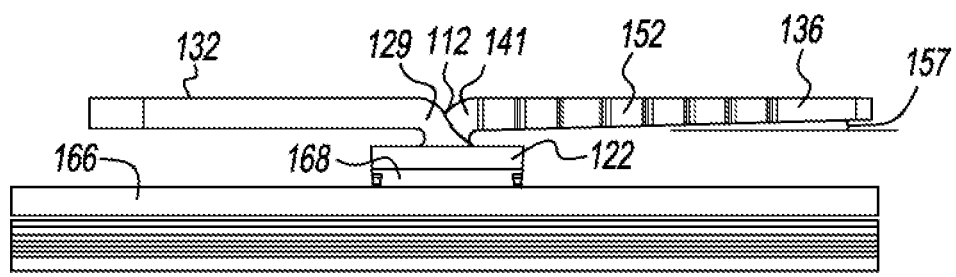
FIG. 12 is a side view of one embodiment of a securement device.
Figure 13:
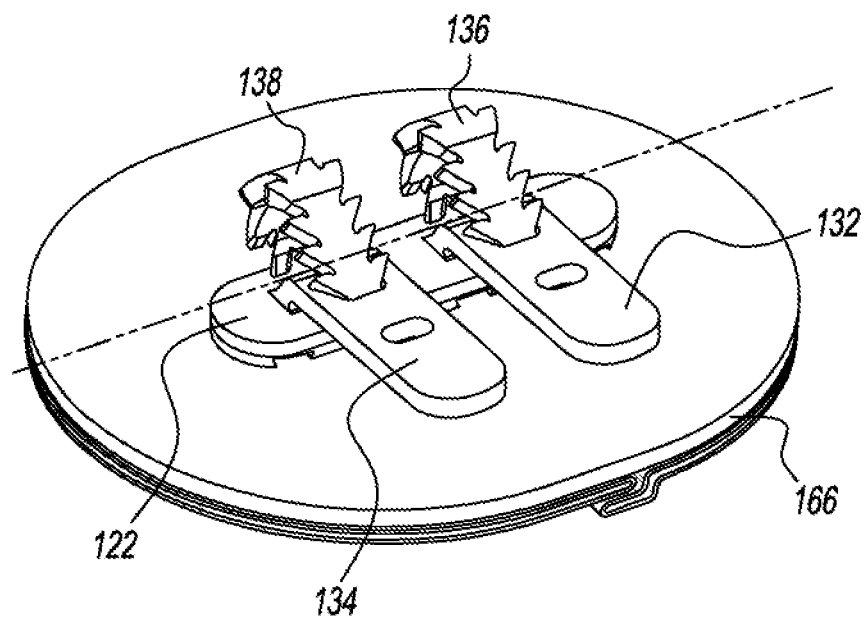
FIG. 13 is an isometric view of one embodiment of a securement device where the free ends of the first and second male straps are inserted into the first aperture of the corresponding first and second female straps, with a small French size tube seated in the securement device.
Figure 14:
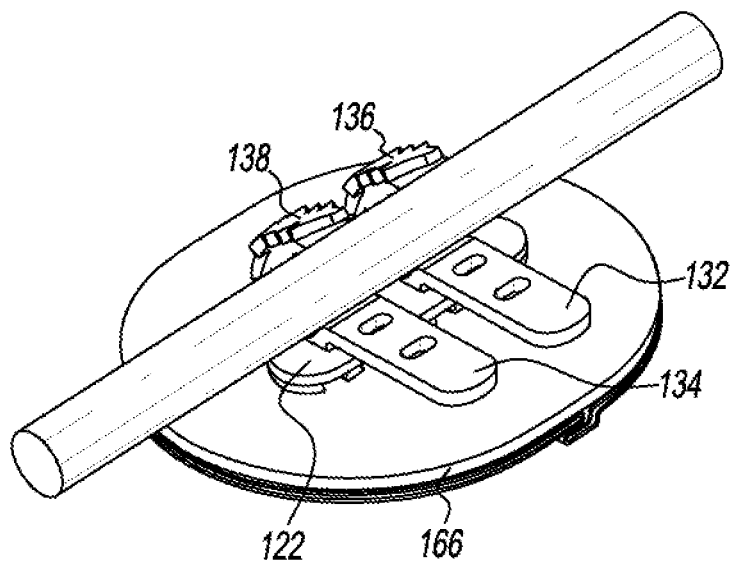
FIG. 14 is an isometric view showing a large French size tube with the first and second male straps being flexed toward the corresponding first and second female straps.

The male straps 36 and 38 have tapered free ends 48 and 50, respectively; and, a series of flared, arrow-shaped, flexible locking members or detents 52 are carried along the lengths of the male straps of a size to pass through the apertures in the female straps in a flexed condition. More particularly, the arrow-like shapes of the flexible locking members 52 allow the flanges thereof to flex while passing through an aperture and then return to an unflexed position to lock the male straps within the female straps. The male straps 36 and 38 have fixed ends 54 and 56, respectively, coupled with the base 22 along a lateral side of the domed platform 40, and the flexible locking members 52 of each strap are carried along a flexible body of the strap extending between the fixed end and the free end with the flexible bodies of the male straps being arcuate in configuration to define engagement portions adjacent the fixed ends as illustrated in FIGS. 8, 9 and 10.

Figure 2:
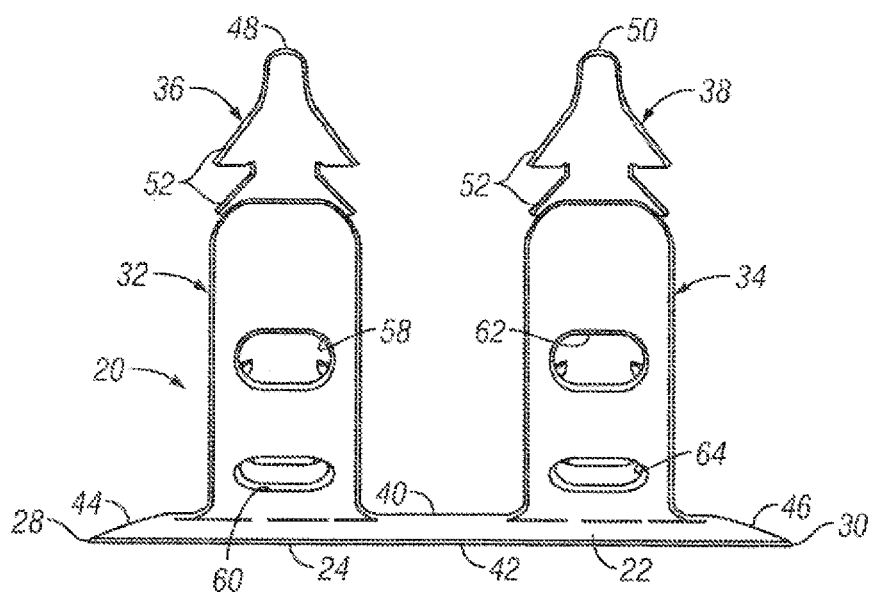

The female straps each have a plurality of apertures therein spaced along the length thereof. As shown in FIG. 2, female straps 32 and 34 each have at least two apertures 58, 60 in female strap 32 and 62, 64 in female strap 34. The lower apertures 60 and 64 looking at FIG. 2 are closer to the base 22 than the upper apertures 58 and 62, and the apertures are sized such that the heights of apertures 60 and 64 are less than the heights of apertures 58 and 62, respectively. The lower heights of the apertures closer to the base provide secure gripping of smaller diameter tubes and also minimize the opportunity for a small diameter tube to be caught therein or pass therethrough.

Figure 6:
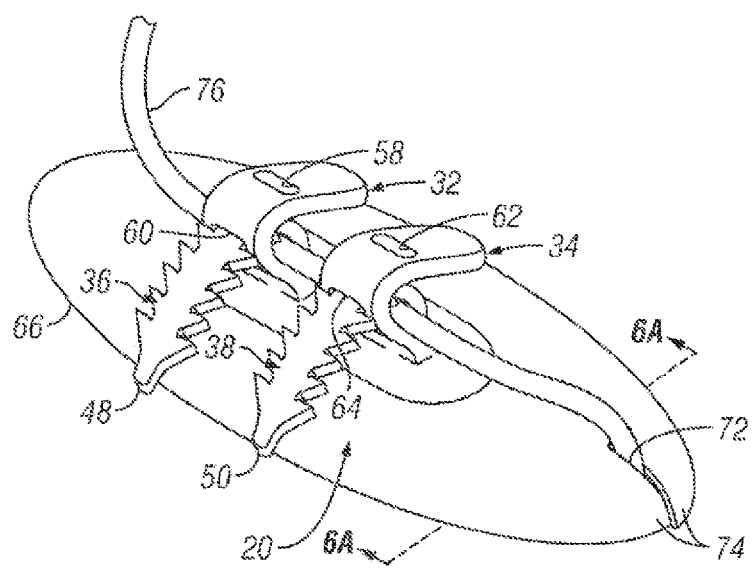
FIG. 6 is a broken perspective view showing the tube holder of FIG. 1 secured to a support surface in the form of an adhesive layer for attachment to the skin and holding a small diameter catheter.
Figure 6A:
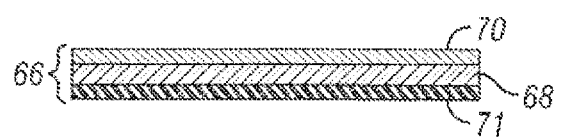
FIG. 6A is a section taken along line 6A-6A of FIG. 6.

The male and female straps join each other at their fixed ends providing a trough with a bottom for receiving and gripping tubes. The base, the gripping members/male and female straps are preferably unitarily, integrally formed of a one-piece soft, low durometer elastomer having a hardness less than or equal to 30 Shore A As shown in FIG. 6, the tube holder 20 includes a support surface or member 66 in the form of an adhesive foundation pad for securement to a patient's body with the base 22 mounted on the support member. As shown in FIG. 6A, the support member 66 is formed of an adhesive layer 68, such as hydrocolloid, bonded to an elastomeric film carrier 70, such as polyurethane, to provide ergonomic and skin-compatible features including moisture balance and elasticity similar to skin, preferably at least 250% elongation, most preferably 300% elongation. The ergonomics result in gradual and uniform transfer of stresses originated from a catheter, and the hydrocolloid on the elastomeric film also provides for extended wear, is hypoallergenic and creates a firm hold even in the presence of perspiration. The adhesive and film combination is preferably transparent or semi-transparent to allow additional infection control by permitting visual detection of any potential underlying skin irritation or infection. The film 70 can be made of polyurethane or any other suitable elastomeric material and as shown, the film 70 is disposed between the bottom surface 42 of base 22 and the layer of hydrocolloid 68. The adhesive layer/pad 66 optimally has an elliptical shape, preferably with a major axis length of twice the length of the base 22 and a major to minor axis ratio of 1.5 to assist in assuring natural movement with the skin. An elliptical shape provides a geometry to assure optimal confirmation to contours of a patient's body which may change shape in multiple planes. The bottom of the adhesive layer 68 is covered with a siliconized release paper 71 which can be plow-folded to facilitate removal thereof prior to placement of the adhesive layer on a patient's skin.

When the tube holder 20 is utilized adjacent a catheter insertion site, the adhesive pad can have a slit or slot 72 therein such that a catheter can extend through the slot as shown in FIG. 6. The adhesive pad adjacent the slot can be used to cover entry of the catheter into the insertion site. When the slot is used, the catheter is inserted at the base of the slot, and the free ends of the ellipse of the adhesive pad which are created by the slot form flaps shown at 74 which overlap. The flaps provide a fully occlusive seal around the catheter which minimizes infection and adds to the positive grip of the catheter thus preventing in-and-out micromotion or pistoning of the catheter at the insertion site which otherwise could lead to distribution of bacterial films and various pathogens. Additionally, the overlapping arrangement of the flaps 74 provides a robust, yet flexible, occlusive seal and protects the skin surface from exposure to fluids or caustic material (e.g. gastric fluids) and further assures a controlled and stable angle of entry of the catheter at the skin/catheter interface to prevent tissue damage through either ischemia (tearing) and/or crushing. The slotted configuration of the adhesive foundation pad 66 coupled with the flexible, soft nature of the base and gripping members enhances the robustness of the occlusive seal with the catheter thereby resisting disruption of the seal. In use, the free ends or flaps of the foundation pad adjacent the slot are wrapped alternately around the catheter such that the hydrocolloid adhesive seals to both the skin of the patient and the foundation pad surfaces to provide the highly occlusive seal against pathogens and guard against in-and-out micromotions that are common with catheter holding devices of the prior art. Since the flaps are integral with the flexible foundation pad and encircle the catheter, the catheter is maintained in proper position at all points from the securement of the tube holder to the skin to the point of catheter insertion into the patient's body.

A small diameter tube 76 is shown in FIG. 6 being gripped by the female straps 32 and 34 and the male straps 36 and 38, the small diameter tube being, for example a 1.9 Fr catheter. The small diameter tube 76 is gripped by passing the free ends 48 and 50 of the male straps 36 and 38, respectively, through the lower, smaller size apertures 60 and 64 in the female straps 32 and 34, respectively, thereby securely gripping the tube 68 and limiting the opportunity for the tube to be drawn through the aperture along with the male strap. As shown in FIG. 8, the small diameter tube 76 is gripped in a trough or space 77 between a female strap 34 and a male strap 38. The space between the engagement portions does not conform completely to the configuration of the tube 76 such that the male and female gripping members/straps provide a channel jaw, pliers type arrangement due to the configurations and thicknesses of the lower segments of the male and female gripping members. That is, as best shown in FIGS. 4 and 5, the thickness of the lower portion of each male member cooperates with the shape of each female gripping member to create a channel-like gripping arrangement therebetween.

FIG. 9 illustrates the securement of an intermediate size tube 82 in space 77 with the male gripping member 38 passing through the lower aperture 64 such that channel lock pliers-type gripping is created by the jaws formed by the engagement portions 78 and 80 of female and male gripping members 34 and 38, respectively.

FIG. 10 illustrates the securement of a large size tube 86 with the male gripping member 38 passing through the upper aperture 62 of the female gripping member to grip the tube with a channel lock plier-gripping arrangement but with the jaws or engagement portions of the gripping members having a configuration more closely approximating the outer configuration of the tube 86 such that engagement portion 78 of female gripping member 34 is arcuate as is the engagement portion 84 of male gripping member 38.

Figure 7:
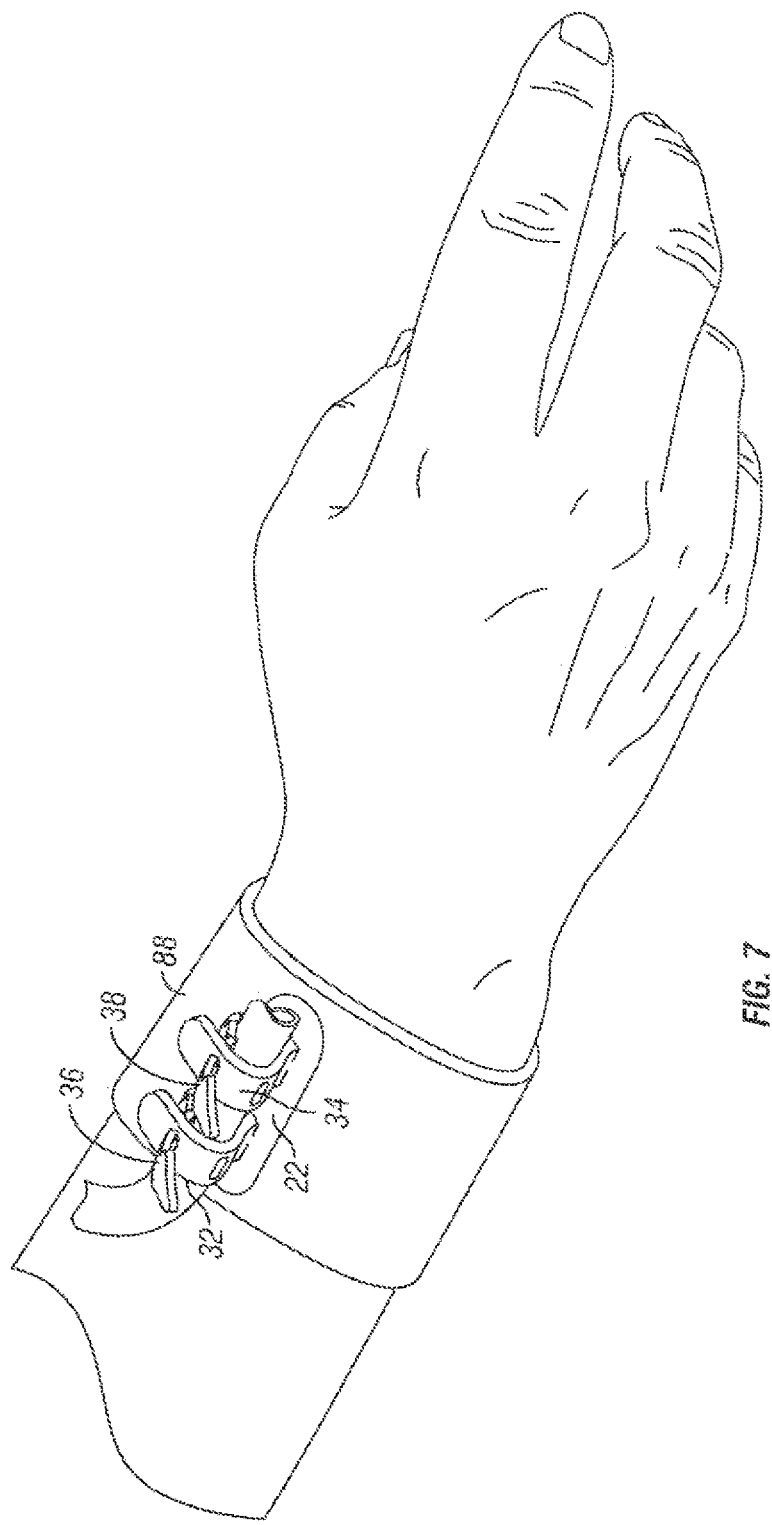
FIG. 7 is a perspective view of the tube holder of FIG. 1 attached to a patient's body via a support surface in the form of a strap and holding a catheter larger in diameter than the catheter in FIG. 6.

FIG. 7 illustrates a tube holder having a base and gripping members as shown in FIGS. 1-5 but where the support surface or foundation pad is formed by a strap 88 surrounding a limb of a patient. With the base 22 being secured, such as by adhesive, to the strap, the use of a strap permits the tube holder to be positioned at various locations on a patient's body as well as on environmental surfaces adjacent a patient. The ends of the strap can be fastened via hook and loop type fasteners (Velcro) or other suitable fasteners such as snaps, buckles and the like or the strap can be elastic with no requirement for fastening of the ends together. Accordingly, the tube holder shown in FIG. 7 is reusable in nature and can be attached to various structures as desired.

The narrowed tips of the male gripping members eases insertion of the male members into a chosen aperture in the female gripping member even while the caregiver is wearing gloves. The thickness of the base and the configuration of the raised platform of the base reduces warping when the tube holder is subjected to stress as a gripping member/strap is pulled tight after insertion through an aperture in an opposing gripping member and further prevents transmission of the stress on the male strap to the patient's skin. The use of an adhesive layer such as hydrocolloid allows the support surface to act as a wound dressing as well as providing securement for the tube holder and further permits incorporation therein of antimicrobial agents to provide an antimicrobial Catheter insertion site dressing. As previously noted, the thickening of the male straps near the base and the curvature of the male straps allow the male straps to come over a tube to be gripped to the female strap like channel lockjaws thus holding small (tiny) catheters. By forming the base and gripping members of the tube holder of a low durometer (less than 30 Shore A and as low as 3 Shore A elastomer), high friction elastomers can be used that grip tubes without kinking and transfer compound twisting and bending forces are transferred uniformly to a patient's skin in that the components of the tube holder act together to transfer significant compound forces to the compound body shapes where the tube holder is applied. With the forces isolated as noted above, the tube holder provides improved and uniform gripping force on tubes while reducing the potential for dislodgement and inadvertent tear-out of the tubes. The sloping surfaces at the longitudinal ends of the base provide a controlled and stable angle of entry of the catheter at a skin-catheter interface thus resisting transmission of leverage forces of the catheter which otherwise might potentially cause tissue damage through ischemia (tearing) and crushing and prevent the catheter from twisting or rotating about the longitudinal axis of the catheter. The use of an adhesive foundation pad, particularly including a hydrocolloid, provides a support surface capable of flexing to accommodate body contours, stretching to match the physiological properties of a patient's skin including swelling from edema and anasarca, facilitates natural movement of a patient's subcutaneous structures with body movement, and assures the skin/adhesive interface remains intact. The gripping arrangement of the tube holder allows a catheter to be easily changed without removing the adhesive support surface from the skin by folding the arrow-shaped flanges of the male gripping members to allow the male gripping members to be pulled backwards through the apertures in the female gripping members while simultaneously providing a positive lock on a catheter such that the catheter cannot be pulled out of the tube holder inadvertently or by a patient using a single hand.

In another embodiment, the tube holder 20 is a securement device 120 that comprises a gripping assembly having a gripping base 122 to a hydrocolloid patch 166. The securement device 120 is made of an amorphous thermoplastic elastomer polymer ("TPE"), which is an elastic material capable of about 870% elongation. TPE also has a very high tear strength value of about 19.3 kilo-Newtons per meter (kN/m). TPE materials exhibit the properties of both plastics and rubbers. Additionally, the natural tribological or frictional nature of the TPE allows for superior gripping to other polymeric materials not represented in previous art. The designed surface area of the interfacing surface of the gripping assembly establishes a large tangential contact area to polymer tubing or polymer coated cable.

Friction, as it pertains to the benefits of the present securement device 120, is stated as follows: friction is an energy-transforming effect generated in the interface between contact objects or a body in contact with another substance in relative motion under action of an external force. The energy-transforming effect results at least from the action of tangential resistance, namely, friction force, occurring in the interface between the securement device 120 and the polymer tubing or polymer coated cable. The novel design features of the securement device 120 coupled with the tribological aspects of the TPE increase the run-in friction of the interface of the securement device 120 and the tubing and/or polymer coated cables.

Run-in friction is an unsteady state friction. It refers to such friction state that the frictional coefficient varies as the sliding time (sliding distance) during the beginnings of relative motion. The use of TPE with these polymeric characteristics increases the mutual attraction of the polymeric substances used in the construction of the tubing and polymer coated cables, and thus increases the coefficient of friction between the contacting polymeric surfaces, thereby minimizing or eliminating a chance occurrence of polymer tubing or polymer coated cables slipping or sliding issues relative to the securement device 120.

The mechanical design features of the securement device 120 coupled with the TPE material enable maximization of the surface contact between the device 120 and the tubing or cable. This in turn minimizes, and even eliminates, the chance occurrence of polymer tubing or polymer coated cables from unintentionally moving or slipping while retained in the securement device 120 and secured to a patient's epidermis.

Referring to FIGS. 11-14, the female straps 132, 134 and male straps 136, 138 can be manufactured in various lengths that can accommodate very small to very large French size tubing and polymer coated cables. These sizes can range from as small as 2 Fr to as large as 47 Fr. Each of the female straps 132, 134 comprise a first aperture 158. The female straps 132, 134 may comprise a second aperture 160. Each of the male straps 136, 138 comprise a spine 137 having a longitudinal axis 139, each spine 137 having a plurality of locking members 152 disposed in pairs, and each pair of locking member 152 disposed symmetrically about the longitudinal axis of the spine 137. Each locking member 152 has a root 151 and a tip 153, the root 151 being attached to the spine 137 such that the locking member 152 projects away from the spine 137, terminating at the tip 153.

Figure 15:
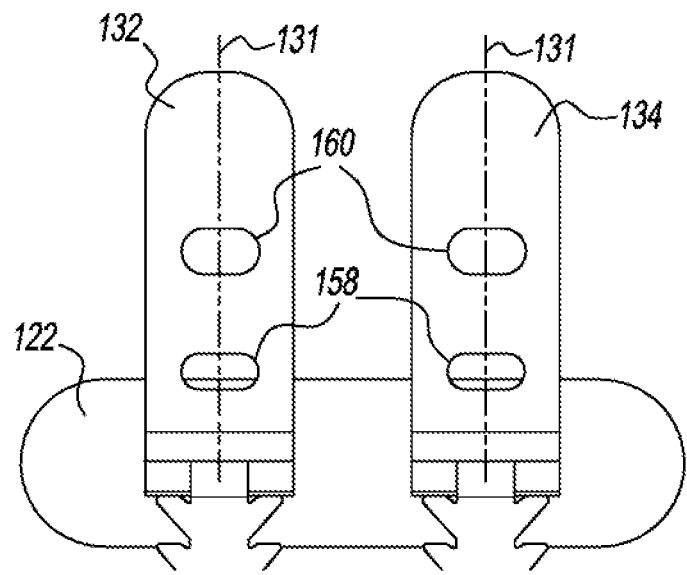
FIG. 15 is an enlarged view of one embodiment of the first and second female straps.

In one embodiment, shown in FIG. 15, each of the female straps 132, 134 has a first aperture 158, a second aperture 160, and a longitudinal axis 131. Each first aperture 158 is spaced about 12 millimeters, center to center along the longitudinal axis 131, from the second aperture 160 on the same female strap 132, 134. The length of each second aperture 160, as measured along the longitudinal axis 131, is about 1.1 millimeters more than the corresponding length of the first aperture 158.

To accommodate and secure relatively small tubing members (about 2 Fr-about 18 Fr), the tubing is placed between the female straps 132, 134 and the male straps 136, 138, and the male straps 136, 138 are inserted into and through the second apertures 160 of the corresponding female strap 132, 134. To accommodate and secure relatively large tubing members (about 18 Fr-about 47 Fr), the tubing is placed between the female straps 132, 134 and the male straps 136, 138, and the male straps 136, 138 are inserted into and through the first apertures 158 of the corresponding female strap 132, 134.

Referring to FIGS. 16-19, when the male straps 136, 138 are threaded though one of the apertures 158, 160, the locking members 152 are forced through the respective aperture 158, 160. The width of each pair of locking members 152, as measured tip 153 to tip 153 perpendicular to the male strap longitudinal axis 139, is slightly larger than the width of each aperture 158, 160, as measured perpendicular to the longitudinal axis 131 of the respective female strap 132, 134. In one exemplary embodiment, this tip 153 to tip 153 measure of the locking member is at least 5 millimeters larger than the width measurement of the corresponding aperture 158, 160. In order for the pair of locking members 152 to be inserted through an aperture 158, 160, the locking members 152 must collapse, or contract, as measured perpendicular to the male strap longitudinal axis 139.

To accommodate this contraction, the root 151 of each locking member 152 comprises a notch 110 (See FIG. 19) that promotes the collapsing motion, or contraction, as the pair of locking members 152 is inserted through the respective aperture 158, 160. This contraction or collapsing action promotes proper mating between the locking members 152 and the apertures 158, 160. The notch 110 also relieves stress and fatigue in the material caused by repeated insertion and removal of the locking members 152 into and from the apertures 158, 160 during proper mating of the female straps 132, 134 and male straps 136, 138. Proper mating promotes maximum surface contact between the securement device 120 and the tube, thereby increasing the friction between these respective surfaces and increasing the holding strength of the securement device 120.

Figure 16:
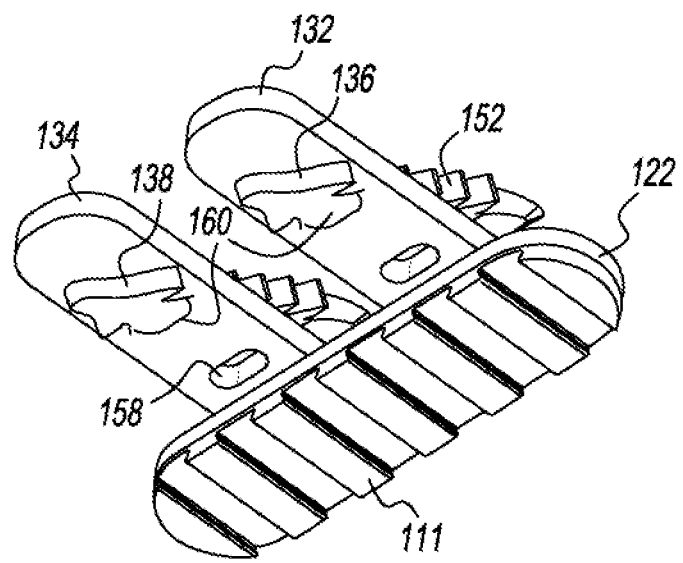
FIG. 16 is a lower isometric view of an embodiment of the securement device having cleats on the base.
Figure 17:
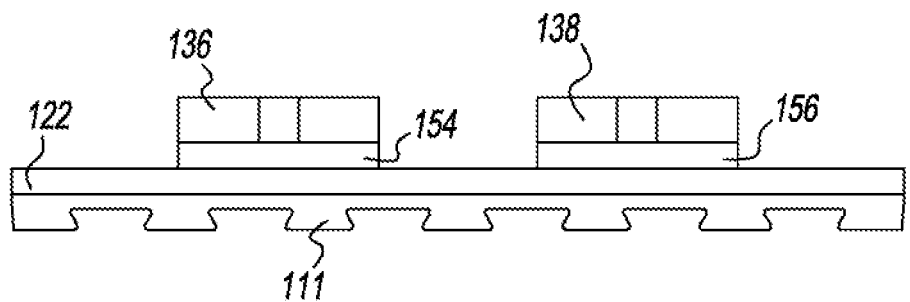
FIG. 17 is a side view of an embodiment of the securement device having cleats on the base.
Figure 18:
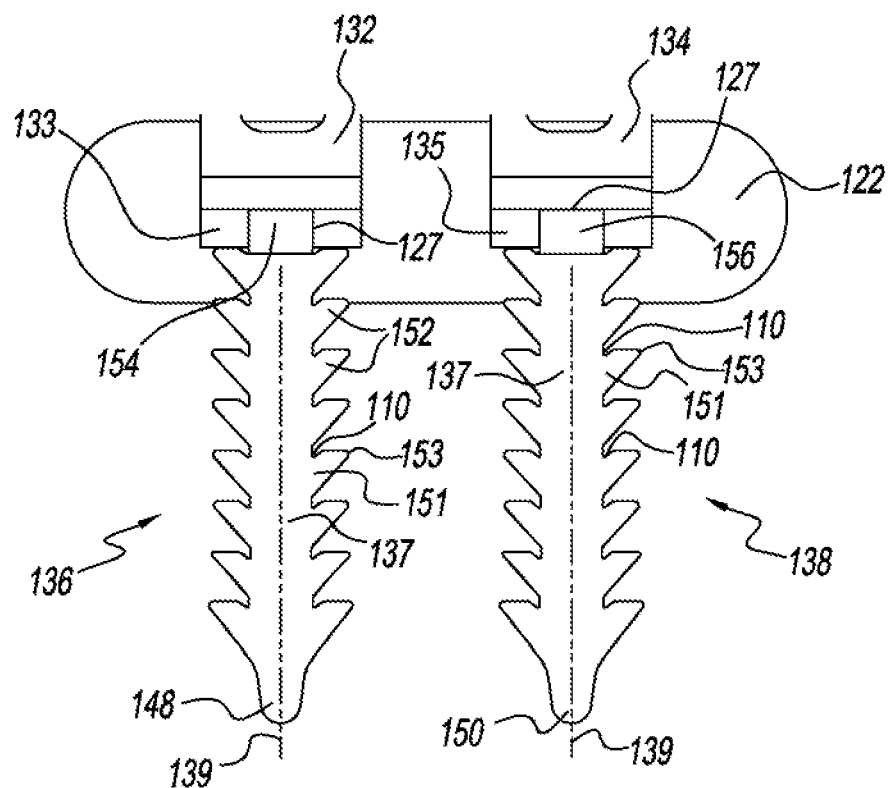
FIG. 18 is an enlarged view of one embodiment of the male straps.

In another embodiment, shown in FIGS. 16-17, the bottom side of the base 122 further comprises a plurality of elongated cleats 111 that provide additional mechanical coupling and chemical bonding strength between the base and the adhesive layer 168, such as epoxy, glue, or other bonding agent used to attach or bond the base 122 to the hydrocolloid patch 166. The cleats 111 may extend fully or partially across the full width of the base 122 on the side of the base 122 that interfaces with the hydrocolloid patch 166. In one embodiment of the cleats 111, the cleats 111 are configured in a dovetail arrangement such that the width of the portion of the cleat 111 that attaches to the base 122 is narrower (as measured substantially perpendicular to the elongated direction of the cleat 111) than the width of the portion of the cleat 111 that interfaces with the hydrocolloid patch 166.

Figure 19:
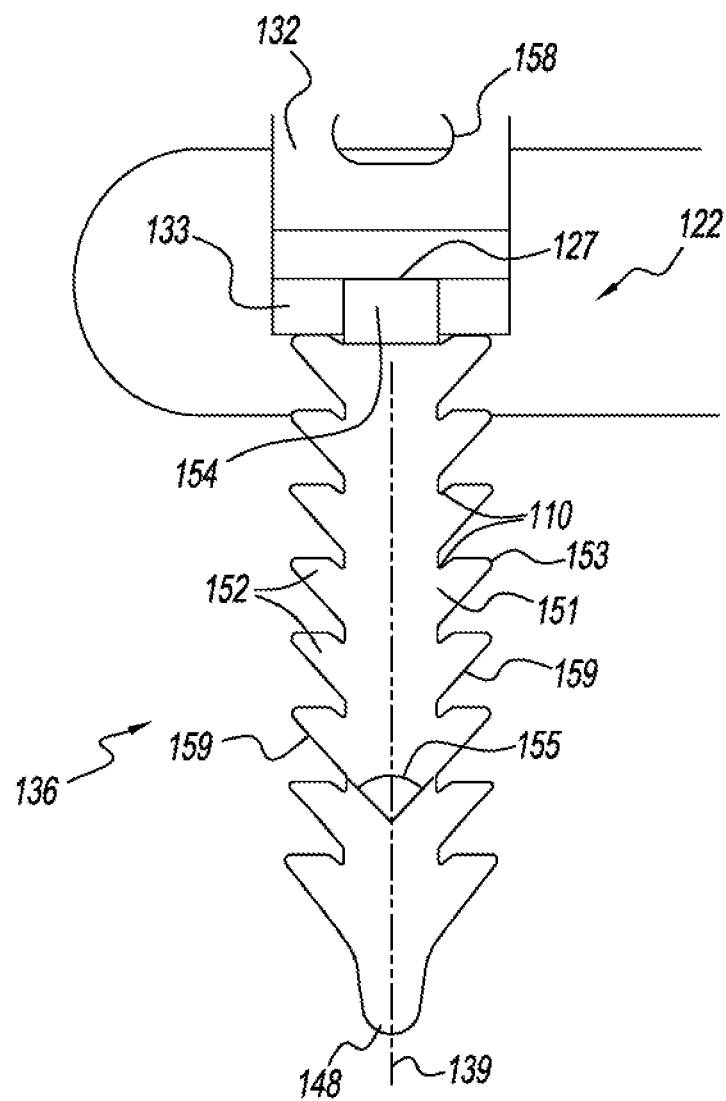
FIG. 19 is an enlarged view of one embodiment of the locking members.

Referring to FIG. 19, the locking members 152, each pair of locking members 152 is oriented such that the angle 155 formed by the leading edges 159 of the respective locking members 152 ranges from about 70 degrees to about 110 degrees. In one embodiment, the angle 155 is about 85 degrees. This angle 155 promotes insertion of each pair of locking members 152 into and through the respective aperture 158, 160 by reducing the resistance force of the pair of locking members 152 passing through the narrower aperture 158, 160.

The pitch of the locking members 152 refers to the ratio of locking members 152 to the length along the male straps 136, 138, as measured along the longitudinal axis 139. It is preferable, but not required, that the pitch of the locking members 152 is about four locking members 152 per 20 millimeters to about 30 millimeters along the male straps 136, 138. In one exemplary embodiment, the pitch of the locking members 152 is four locking members 152 per 25 millimeters of length along the male straps 136, 138. This spacing is optimized to accommodate tubing members of a variety of French sizes, ranging from as small as 2 Fr to as large as 47 Fr.

Referring again to FIG. 12, the male straps 136, 138 are tapered such that the fixed ends 154, 156 each of the male straps 136, 138 is thicker than the free ends 148, 150. The angle of taper 157 ranges from about 1 degree to about 5 degrees. In one embodiment, the angle of taper 157 is about 2 degrees. This angle of taper 157 is optimized to facilitate threading of the male straps 136, 138 through the respective female straps 132, 134.

Figure 20:
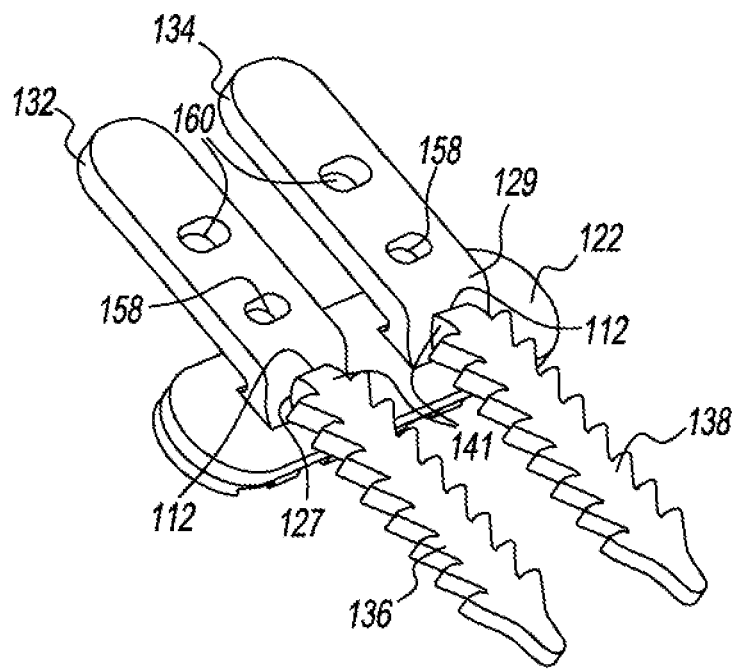
FIG. 20 is an isometric view of one embodiment of the securement device.
Figure 21:
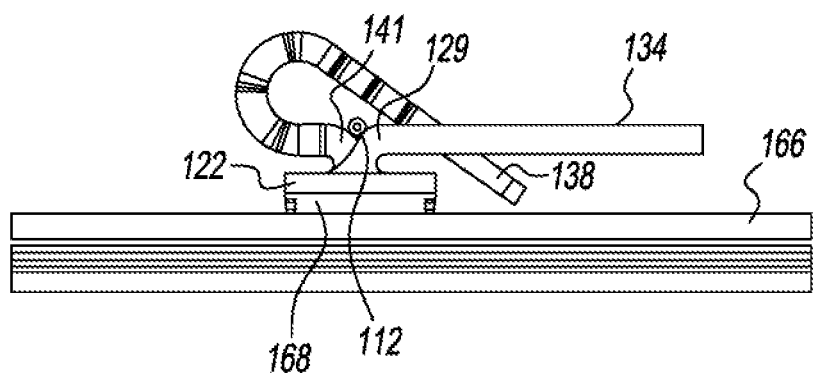
FIG. 21 is a side view of the embodiment shown in FIG. 13.

Referring to FIGS. 20-21, the arrangement and configuration of the female straps 132, 134 and the male straps 136, 138 is optimized to maximize the surface contact area between the securement device 120 and the tube or cable being secured. To this end, the securement device 120 comprises a seating zone 112 for seating the tube or cable being secured. The fixed ends 133, 135 of the respective female straps 132, 134 comprise a curved portion 129 adapted to orient the unsecured female straps 132, 134 substantially parallel to the base 122. The fixed ends 133, 135 further comprise a recess 127 for receiving the fixed ends 154, 156 of the respectively mating male straps 136, 138. The respective fixed ends 154, 156 of the male straps 136, 138 also comprise a curved portion 141 adapted to orient the unsecured male straps 136, 138 substantially parallel to the base 122. The fixed ends 154, 156 of the male straps 136, 138 are seated in, or mated with, the recess 127 in the fixed ends 133, 135 of the female straps 132, 134, and all of the fixed ends 133, 135, 154, 156 are connected to the base 122. In this configuration, the curved portions 129, 141 form or define a crease that acts as the seating zone 112 for seating the tube or cable being secured by the securement device 120.

Figure 22:
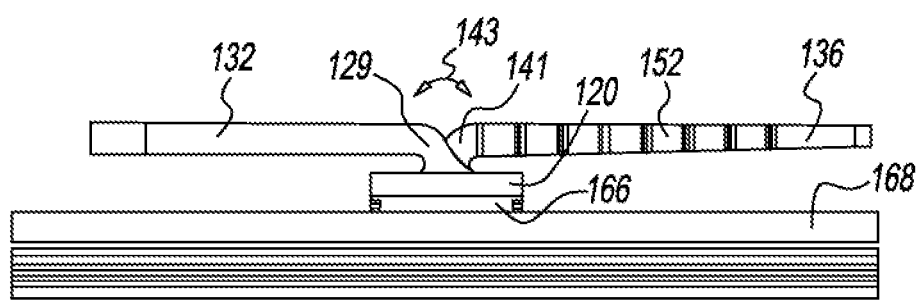
FIG. 22 is a side view of one embodiment of a securement device showing an unsecured first male strap and an unsecured first female strap.

Referring to FIG. 22, the curved portions 129, 141 are configured such that the lie angle 143 formed by the unsecured female straps 132, 134 and the unsecured male straps 136, 138 is in the range of about 160 degrees to about 200 degrees. In another embodiment, this lie angle 143 is about 180 degrees. This orientation of the unsecured straps 132, 134, 158, 160 reduces mechanical occluding of the tubing or cables enclosed by the securement device 120. It also reduces the possibility of the unsecured straps 132, 134, 158,

160 inadvertently snagging or entangling loose articles such as bedding, clothing, or unrelated tubing, hoses, cables, or other articles.

A method of securing a catheter to a patient's body utilizing a tube holder as described above includes the steps of securing the support surface to the patient's body, positioning the catheter between at least one pair of the male and female gripping members in the trough defined therebetween by the engagement portions thereof, selecting one of the apertures in the female gripping member based on the size of the catheter, inserting the tapered free end of the male gripping member in the selected aperture and pulling the male gripping member through the selected aperture to grip the catheter there between, it being noted that when multiple pairs of male/female gripping members are utilized, the gripping members are tightened sequentially.

The foregoing embodiments are merely representative of the securement device and not meant for limitation of the invention. For example, persons skilled in the art would readily appreciate that there are several embodiments and configurations of male and female straps, and other components will not substantially alter the nature of the securement device. Likewise, elements and features of the disclosed embodiments could be substituted or interchanged with elements and features of other embodiments, as will be appreciated by an ordinary practitioner. Consequently, it is understood that equivalents and substitutions for certain elements, embodiments, and components set forth above are part of the invention described herein, and the true scope of the invention is set forth in the claims below.

What is claimed is:

1. A securement device for securing a medical tube or cable, comprising:
    a base having a length, a width, a top side, and a bottom side;
    a female strap extending substantially transversely from the base, the female strap having a length extending from a fixed end attached to the top side of the base to a free end, and a plurality of apertures spaced along the length of the female strap, the fixed end comprising a curved portion;
    a male strap extending substantially transversely from the base, the male strap having a length extending from a fixed end attached to the top side of the base to a free end, the fixed end comprising a curved portion, and the male strap comprising a plurality of flexible locking members disposed in pairs along the length of the male strap;
    wherein the locking members on the male strap are configured for releasably mating with the apertures in the female strap; and
    the respective male and female fixed ends disposed in a mating, overlapping orientation such that the curved portion of the fixed end of the female strap and the curved portion of the fixed end of the male strap define a crease for seating the tube or cable.

2. The securement device of claim 1, wherein the female strap comprises a first aperture and a second aperture, the first aperture being located along the length of the strap at a location closer to the base than that of the second aperture, the first aperture having a shorter length than the second aperture.

3. The securement device of claim 1, wherein each of the locking members further comprises an angled leading edge.

4. The securement device of claim 1, wherein the male strap comprises an angle of taper such that the fixed end of the male strap is thicker than the free end of the respective male strap.

5. The securement device of claim 1, wherein the bottom side of the base comprises a plurality of elongated cleats extending at least partially across the width of the base, the cleats configured in a dovetail arrangement, wherein the width of the cleat is measured substantially perpendicular to the elongated direction of the cleat.

6. The securement device of claim 5, wherein each of the locking members further comprises an angled leading edge.

7. The securement device of claim 5, wherein the male strap comprises an angle of taper such that the fixed end of the male strap is thicker than the free end of the respective male strap.

8. The securement device of claim 5, wherein the female strap comprises a first aperture and a second aperture, the first aperture being located along the length of the strap at a location closer to the base than that of the second aperture, the first aperture having a shorter length than the second aperture.

9. The securement device of claim 8, wherein each of the locking members further comprises an angled leading edge.

10. The securement device of claim 8, wherein the male strap comprises an angle of taper such that the fixed end of the male strap is thicker than the free end of the respective male strap.

11. A securement device for securing a medical tube or cable, comprising:
    a base having a length, a width, a top side, and a bottom side;
    a first female strap extending substantially transversely from the base, the first female strap having a length extending from a fixed end attached to the top side of the base to a free end, and a plurality of apertures spaced along the length of the first female strap, the fixed end comprising a curved portion having a recess;
    a second female strap extending substantially transversely from the base at a position longitudinally spaced from the first female strap, the second female strap having a length extending from a fixed end attached to the top side of the base to a free end, and a plurality of apertures therein spaced along the length of the second female strap, the fixed end comprising a curved portion having a recess;
    a first male strap extending substantially transversely from the base, the first male strap having a length extending from a fixed end attached to the top side of the base to a free end, the fixed end comprising a curved portion, and the first male strap comprising a plurality of flexible locking members disposed in pairs along the length of the first male strap; and
    a second male strap extending substantially transversely from the base at a position longitudinally spaced from the first male strap, the second male strap having a length extending from a fixed end attached to the top side of the base to a free end, the fixed end having a curved portion, and the second male strap comprising a plurality of flexible locking members disposed in pairs along the length of the second male strap;
    the locking members on the first and second male straps are configured for releasably mating with the apertures in the first and second female straps, respectively;
    the respective male and female fixed ends disposed in a mating, overlapping orientation such that the curved portion of the fixed end of each female strap and the curved portion of the fixed end of the corresponding male strap defining a crease for seating the tube or cable.

12. The securement device of claim 11, wherein each of the first and second female straps comprises a first aperture and a second aperture, the first aperture being located along the length of each respective strap at a location closer to the base than that of the second aperture, the first aperture having a shorter length than the second aperture.

13. The securement device of claim 11, wherein each of the locking members further comprises an angled leading edge.

14. The securement device of claim 11, wherein each of the first and second male straps comprises an angle of taper such that the fixed end of the respective male straps is thicker than the free ends of the respective male straps.

15. The securement device of claim 11, wherein the bottom side of the base comprises a plurality of elongated cleats extending at least partially across the width of the base, the cleats configured in a dovetail arrangement, wherein the width of the cleat is measured substantially perpendicular to the elongated direction of the cleat.

16. The securement device of claim 15, wherein each of the locking members further comprises an angled leading edge.

17. The securement device of claim 15, wherein each of the first and second male straps comprises an angle of taper such that the fixed end of the respective male straps is thicker than the free ends of the respective male straps.

18. The securement device of claim 15, wherein each of the first and second female straps comprises a first aperture and a second aperture, the first aperture being located along the length of each respective strap at a location closer to the base than that of the second aperture, the first aperture having a shorter length than the second aperture.

19. The securement device of claim 18, wherein each of the locking members further comprises an angled leading edge.

20. The securement device of claim 18, wherein each of the first and second male straps comprises an angle of taper such that the fixed end of the respective male straps is thicker than the free ends of the respective male straps.

* * * * *